United States Patent [19]
Mohr et al.

[11] Patent Number: 6,121,465
[45] Date of Patent: Sep. 19, 2000

[54] PROCESS FOR PRODUCTION DROSPIRENONE AND INTERMEDIATE PRODUCTS OF THE PROCESS

[75] Inventors: Jörg-Thorsten Mohr; Klaus Nickisch, both of Berlin, Germany

[73] Assignee: Schering Aktiengesellschaft, Berlin, Germany

[21] Appl. No.: 09/242,334

[22] PCT Filed: Aug. 11, 1997

[86] PCT No.: PCT/EP97/04342

§ 371 Date: Feb. 11, 1999

§ 102(e) Date: Feb. 11, 1999

[87] PCT Pub. No.: WO98/06738

PCT Pub. Date: Feb. 19, 1998

[30] Foreign Application Priority Data

Aug. 12, 1996 [DE] Germany .................. 196 33 685

[51] Int. Cl.⁷ .................................... C07D 307/94
[52] U.S. Cl. ............................................. 549/265
[58] Field of Search ................... 549/265; 568/817

[56] References Cited

U.S. PATENT DOCUMENTS

| | | | |
|---|---|---|---|
| 4,416,985 | 11/1983 | Petzoldt et al. | 435/58 |
| 4,435,327 | 3/1984 | Petzoldt et al. | 260/397.5 |
| 5,106,995 | 4/1992 | Plotkin | 549/273 |

FOREIGN PATENT DOCUMENTS

| | | |
|---|---|---|
| 0051143 | 5/1982 | European Pat. Off. . |
| 0075189 | 3/1983 | European Pat. Off. . |
| 9014344 | 11/1990 | WIPO . |

OTHER PUBLICATIONS

Bittler et al., "Synthesis of Spirorenone–A Novel Highly Active Aldosterone Antagonist," *Angewandte Chemie. International Edition*, vol. 21, Issue 9, pp. 696–697 (1982).

*Primary Examiner*—Ba K. Trinh
*Attorney, Agent, or Firm*—Millen, White, Zelano & Branigan

[57] ABSTRACT

Process for the production of drospirenone (6β, 7β; 15β, 16β-dimethylene-3-oxo-17α-pregn-4-ene-21, 17-carbolactone, DRSP) (1) and 7α-(3-hydroxy-1-propyl)-6β, 7β; 15β, 16β-dimethylene-5β-androstane-3β, 5, 17β-triol (ZK 92836) and 6β, 7β; 15β, 16β-dimethylene-5β-hydroxy-3-oxo-17α-androstane-21, 17-carbolactone (ZK 90965) as intermediate products of the process.

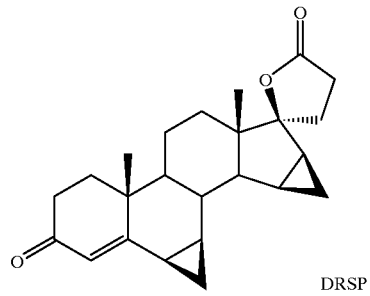

DRSP

17 Claims, No Drawings

PROCESS FOR PRODUCTION DROSPIRENONE AND INTERMEDIATE PRODUCTS OF THE PROCESS

This application is a 371 of PCT/EP97/04342 filed Nov. 11, 1997.

The invention relates to a process for the production of drospirenone (6β, 7β; 15β, 16β-dimethylene-3-oxo-17α-pregn-4-ene-21, 17-carbolactone, DRSP) and 7α-(3-hydroxy-1-propyl)-6β, 7β; 15β, 16β-dimethylene-5β-androstane-3β, 5, 17β-triol (ZK 92836) and 6β, 7β; 15β, 16β-dimethylene-5β-hydroxy-3-oxo-17α-androstane-21, 17-carbolactone (ZK 90965) as intermediate products of the process.

Drospirenone (6β, 7β; 15β, 16β-dimethylene-3-oxo-17α-pregn-4-ene-21, 17-carbolactone, DRSP, INN) has been known for some time as a steroidal active ingredient (DE 26 52 761 C2 and DE 30 22 337 A1), and the production of the last 4 steps is carried out in a single-pot reaction; in which after dimethylene propinol ZK 34506 is hydrogenated, none of the intermediate stages dimethylene propanol and 5-β—OH-DRSP that are passed through are isolated (see diagram below).

The dimethylene propinol ZK 34506 is hydrogenated in tetrahydrofuran with hydrogen on palladium-carbon into dimethylene propanol ZK 92836. The hydrogenating solution that is thus obtained, which contains propanol ZK 92836 as the main product and varying proportions of lactol, is reacted without isolation and intermediate working-up to drospirenone ZK 30595 (DRSP).

For this purpose, a change of solvent from tetrahydrofuran to dimethylformamide first takes place and then the propanol is oxidized at 40° C. with an excess of 3.7 equivalents of pyridinium dichromate (PDC) to a mixture of DRSP and 5—β—OH—DRSP. The 5—β—OH group in the oxidation product is labile compared to acids, Lewis acids and basic conditions at elevated temperatures, since in all cases, a more thermodynamically stable product is obtained with the formation of the Δ-4, 5-unsaturated ketone in the drospirenone. The elimination of the β-OH group in the 5—β—OH—DRSP results in more thermodynamically stable drospirenone, and it was not possible to suppress it.

The mixture generally contains differing proportions of the two components, whereby 5—β—OH—DRSP is generally present as a main component at a ratio of 2-3:1. In the last stage of the single-pot sequence, the two-component mixture is converted by adding semi-concentrated hydrochloric acid into the DRSP, crude.

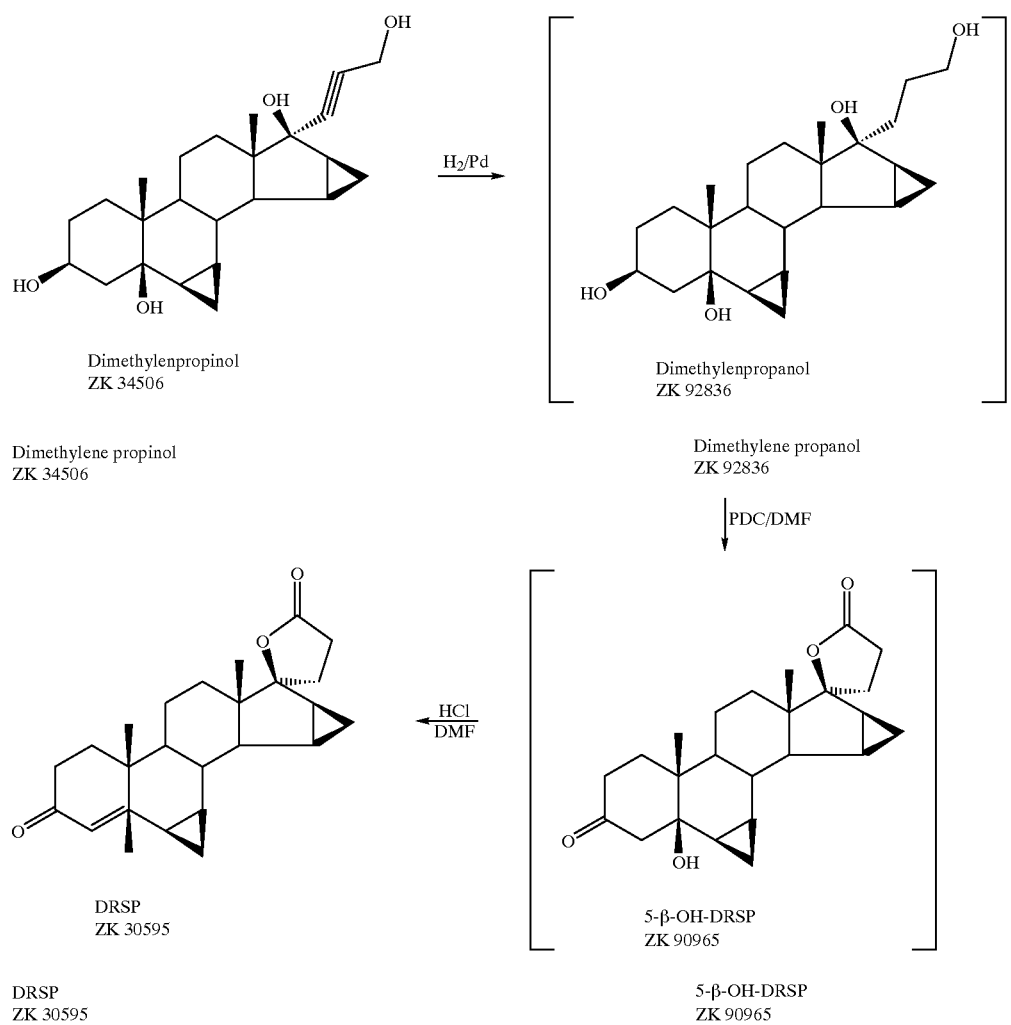

Dimethylene propinol
ZK 34506

Dimethylene propanol
ZK 92836

DRSP
ZK 30595

5-β-OH-DRSP
ZK 90965

In the table below, the last four operating preparations are summarized.

| Preparation | Yield, crude (%) | Purity (100% Method) |
|---|---|---|
| 537201 | 57.2 | 98.9 |
| 202 | 63.7 | 99.09 |
| 203 | 46.5 | 99.18 |
| 204 | 58.3 | 98.81 |
| Total | Mean Yield: 56.4 | Mean Purity: 98.9 |

By the means of all operational preparations, starting from dimethylene propinol, a theoretical yield of 56% DRSP, crude at an HPLC purity of 98.9%, is achieved.

The object of the invention is the provision of a new production process for drospirenone, which is more selective and simpler in execution than that from the prior art and, in addition, is ecological (savings of a chromium trioxide oxidation).

This object is achieved according to the teaching of the claims.

The invention contains a process for the production of drosporenone (6β, 7β; 15β, 16β-dimethylene-3-oxo-17α-pregn-4-ene-21, 17-carbolactone, DRSP)

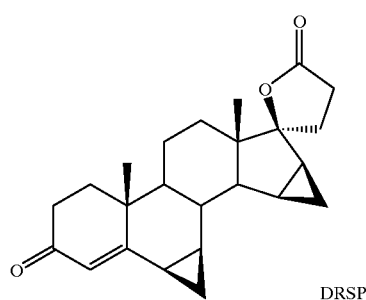

DRSP by catalytic hydrogenation of 17α-(3-hydroxy-1-propynyl)-6β, 7β; 15β, 16β-dimethylene-5-androstane-3β, 5, 17β-triol (ZK 34506)

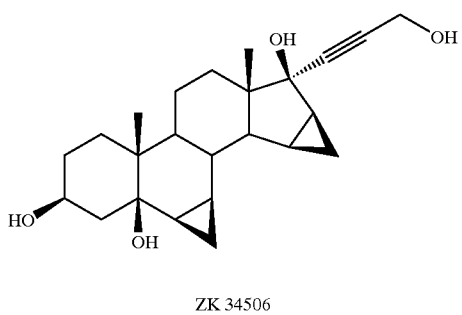

ZK 34506 into 7α-(3-hydroxy-1-propyl)-6β, 7β; 15β, 16β-dimethylene-5β-androstane-3β, 5, 17β-triol (ZK 92836)

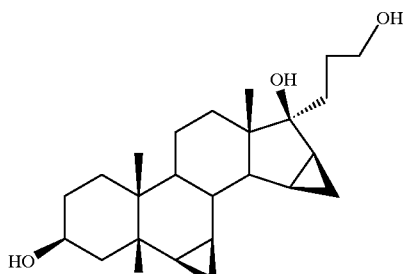

ZK 92836 then oxidation with use of commercially available ruthenium salts, such as $RuCl_3$, $RuO_2$, $KRuO_4$, $K_2RuO_4$, but preferably in the presence of catalytic amounts of $RuCl_3$ (1 mol %) and conventional, simple oxidizing agents such as butyl hydroperoxide, N-methyl-morpholine-N-oxide, $M_2S_2O_8$ (M=Na, K), MXOy (M=Li, Na, K; X=B, Cl, Br, 1:y=1–4), but preferably 1–3 equivalents of $NaBrO_3$, in solvents such as acetonitrile, chloroform, methylene chloride, carbon tetrachloride, water, tetrahydrofuran, tert-butanol, ethyl acetate or combinations thereof, but preferably in an acetonitrile-water mixture in the composition of acetonitrile:water=1:1, in 6β, 7β; 15β, 16β-dimethylene-5β-hydroxy-3-oxo-17α-androstane-21, 17-carbolactone (ZK 90965)

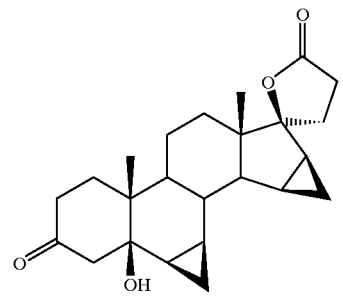

ZK 90965 and subsequent dehydration.

As a key reaction, the invention contains the ruthenium-catalyzed oxidation of dimethylene propanol ZK 92836 to 5—β—OH—DRSP ZK 90965 and the subsequent elimination of water to drospirenone ZK 30595 in a two-stage process.

Analogously to the known process from the prior art, in the process according to the invention, dimethylene propinol ZK 34506 is hydrogenated with hydrogen on palladium-carbon into tetrahydrofuran. The hydrogenating solution is then subjected to a change of solvent, from tetrahydrofuran to acetonitrile. The acetonitrile solution is oxidized with a catalytic amount of ruthenium trichloride (1 mol %) and 3 equivalents of sodium bromate at 40°–60° C., specifically to 5—β—OH—DRSP. Despite the significant liability of 5—β—OH—DRSP compared to acids, Lewis acids, such as, for example, chromium compounds in old operating processes, strong bases or high temperatures, which in all cases can be attributed to the high driving force to form the more thermodynamically stable Δ-4, 5-unsaturated ketone, the selective synthesis of 5—β—OH—DRSP can be accomplished under the selected reaction conditions without a formation of drospirenone being observed. The 5—β—OH—DRSP can be isolated from the reaction solution by a precipitation of water that is simple to implement (operationally).

The yields are in the range of 68% to 75% via the two stages: hydrogenation and then oxidation.

From some tests, it is known that in the case of acidic action, drospirenone can be decomposed with acidic action via two reaction routes. For one thing, under acidic conditions, the drospirenone is easily converted into epimeric isolactone ZK 35096.

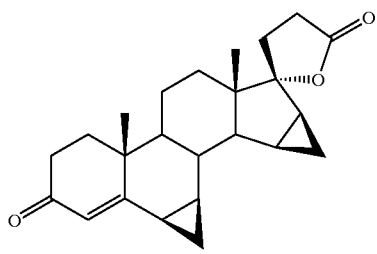

ZK 35096

The second by-product is produced by an HCl attack on the 6, 7-methylene group, which results in ring opening product ZK 95673.

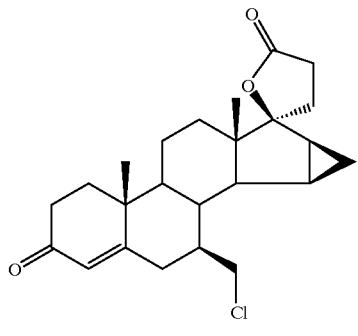

ZK 95673

Both by-products are pushed back under the reaction conditions of the new process to the extent that they can be observed only on an order of magnitude of<0.2%.

In the elimination, a yield of 96% of theory is achieved. The total yield of the new process thus lies in the range of 65% to 72% of theory.

Another very basic advantage of the process according to the invention compared to the prior art lies in the range of ecology. It has been possible to replace the previously used toxic chromium compounds, which so far have been used in the form of pyridinium dichromate salts for oxidation and must subsequently be disposed of in the form of their solutions, by catalytic amounts of a metal. In addition, it is possible to recycle the used acetonitrile-water mixture by azeotropic distillation, so that also no danger to the environment is likely.

The invention also contains the intermediate products 7α-(3-hydroxy-1-propyl)-6β, 7β; 15β, 16β-dimethylene-5β-androstane-3β, 5, 17β-triol (ZK 92836) and 6β, 7β; 15β, 16β-dimethylene-5β-hydroxy-3-oxo-17α-androstane-21, 17-carbolactone (90965).

EXAMPLE

6β, 7β; 15β, 16β-Dimethylene-5β-hydroxy-3-oxo-17α-androstane-21, 17-carbolactone 50 g of 17α-(3-hydroxy-l-propynyl)-6β, 7β; 15β, 16β-dimethylene-5β-androstane-3β, 5, 17β-triol is hydrogenated into 1000 ml of THF in the presence of 10 g of palladium on carbon (10%) and 3 ml of pyridine until 2 equivalents of hydrogen are taken up. Then, the catalyst is filtered off, and the solution is evaporated to the dry state, whereby 52.7 g of 7α-(3-hydroxy-1-propyl)-6β, 7β; 15β, 16β-dimethylene-5β-androstane-3β, 5, 17β-triol is obtained, which is further reacted without purification.

50.2 g of 7α-(3-hydroxy-1-propyl)-6β, 7β; 15β, 16β-dimethylene-5β-androstane-3β, 5, 17β-triol is suspended in 250 ml of acetonitrile and heated to 45° C. 0.52 g of ruthenium trichloride, dissolved in 10 ml of water, and 62.46 g of sodium bromate, dissolved in 250 ml of water, are added in drops to the above. It is stirred for 2 more hours at 50° C., and the solution is then quenched by adding 1000 ml of water. 200 ml of ethyl acetate is added, the phases are separated and then the aqueous phase is extracted with 600 ml of ethyl acetate. The combined organic phases are dried on sodium sulfate and then evaporated to the dry state. In this case, 43.44 g of 6β, 7β; 15β, 16β-dimethylene-5β-hydroxy-3-oxo-17α-androstane-21, 17-carbolactone is obtained as crude product, 35.7 g of 6β, 7β; 15β, 16β-dimethylene-5β-hydroxy-3-oxo-17α-androstane-21, 17-carbolactone with a melting point of 216°–218° C. is obtained by recrystallization from acetone-isoether. The rotation is approximately –65.6° C. (sodium line, c=1.02 in CHC13).

6β, 7β; 15β, 16β-Dimethylene-3-oxo-17α-pregn-4-ene-21, 17-carbolactone 28 g of 6β, 7β; 15β, 16β-dimethylene-5β-hydroxy-3-oxo-17α-androstane-21, 17-carbolactone is suspended in 280 ml of THF and then mixed with 10 mol % of 1.5 g of p-toluenesulfonic acid. After 30 minutes, 125 ml of saturated NaCl solution and 8.2 ml of 1N NaOH solution are added. After phase separation, the organic phase is dried on sodium sulfate and evaporated to the dry state, whereby 25.67 g of 6β, 7β; 15β, 16β-dimethylene-3-oxo-17α-pregn-4-ene-21, 17-carbolactone is obtained as crude product, whose purity is approximately 93% according to HPLC determination.

Further purification can be done by chromatography.

The melting point of the chromatographed substance is approximately 197.5°–200° C.

We claim:

1. A process for the production of 6β, 7β; 15β, 16β-dimethylene-3-oxo- 17α-pregn-4-ene-21, 17-carbolactone,

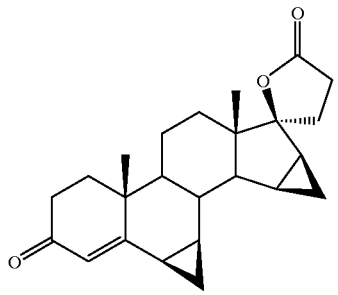

comprising, catalytically hydrogenating 17α-(3-hydroxy-1-propynyl)-6β, 7β; 15β, 16β-dimethylene-5-androstane-3β, 5, 17β-triol of Formula I

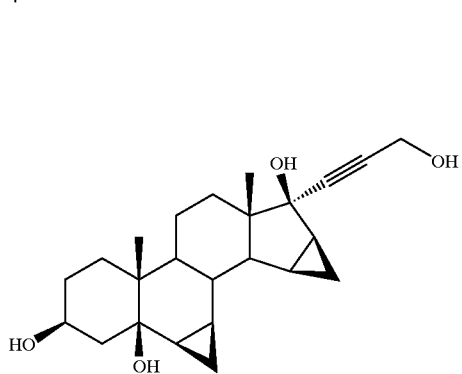

I into 7α-(3-hydroxy-1-propyl)-6β, 7β; 15β, 16β-dimethylene-5β-androstane-3β, 5, 17β-triol of Formula II

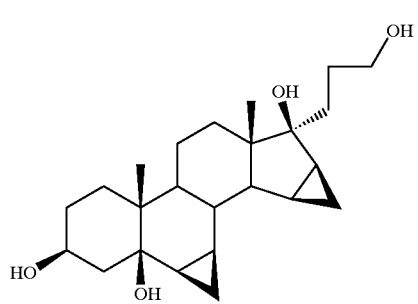

II oxidizing the compound of Formula II in the presence of ruthenium salt to form 6β, 7β; 15β, 16β-dimethylene-5α-hydroxy-3-oxo-17α-androstane-21, 17-carbolactone of Formula III

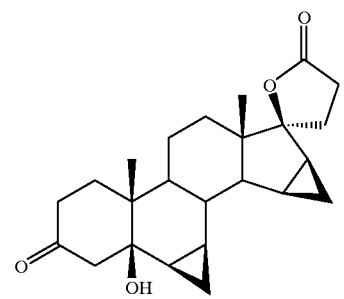

III and dehydrating the latter.

2. 6β, 7β; 15β, 16β-dimethylene-5β-hydroxy-3-oxo-17α-androstane-21, 17-carbolactone

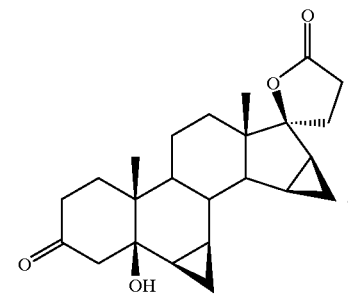

3. A process for the production of 6β, 7β; 15β, 16β-dimethylene-3-oxo-17α-pregn-4-ene-21, 17-carbolactone,

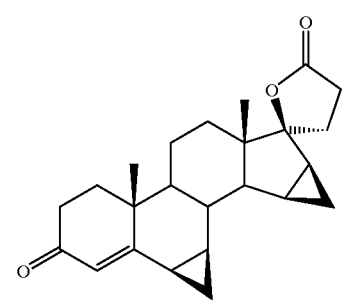

comprising dehydrating a compound of Formula III,

III

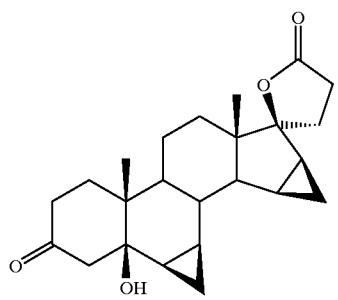

which was made by oxidizing in the presence of a ruthenium salt a compound of Formula II,

II

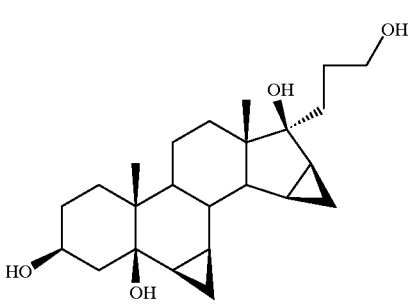

which was made by catalytically hydrogenating a compound of Formula I

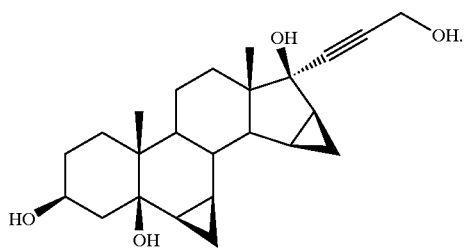

4. A process for the production of the compound of claim 2, comprising oxidizing in the presence of a ruthenium salt a compound of Formula II

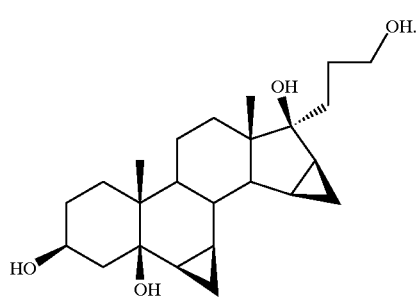

5. A process for the production of the compound of claim 2, comprising oxidizing in the presence of a ruthenium salt a compound of Formula II,

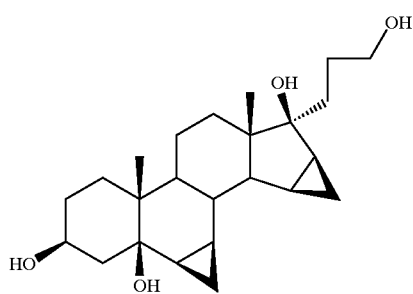

which was made by catalytically hydrogenating a compound of Formula I:

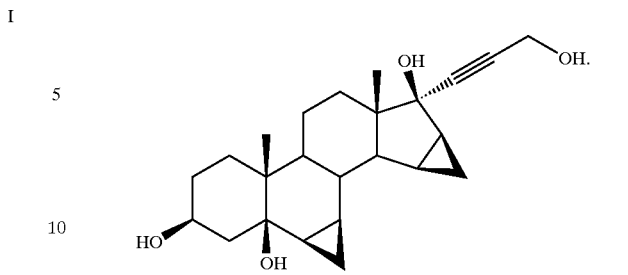

6. The process of claim 1, wherein said catalytic hydrogenating is performed in tetrahydrofuran with hydrogen on palladium-carbon.

7. The process of claim 1, wherein said compound of Formula II is reacted without isolation and intermediate working-up to prepare drospirenone.

8. The process of claim 1, wherein said oxidizing is performed in dimethylformamide at about 40° C. with an excess of 3.7 equivalents of pyridinium dichromate.

9. The process of claim 1, wherein said dehydrating is performed by adding semi-concentrated hydrochloric acid.

10. The process of claim 1, wherein said ruthenium salt is $RuCl_3$, $RuO_2$, $KRuO_4$ or $K_2RuO_4$.

11. The process of claim 1, wherein said oxidizing is performed in the presence of a catalytic amount of $RuCl_3$ and an oxidizing agent.

12. The process of claim 1, wherein said oxidizing is performed in the presence of, as oxidizing agent, butyl hydroperoxide, N-methyl-morpholine-N-oxide, $M_2S_2O_8$, wherein M is Na or K, or $MXO_y$, wherein M is Li, Na or K, X is B, Cl, Br, or I, and y is 1–4.

13. The process of claim 12, wherein said oxidizing agent is 1–3 equivalents of $NaBrO_3$.

14. The process of claim 1, wherein said oxidizing is performed in the solvent acetonitrile, chloroform, methylene chloride, carbon tetrachloride, water, tetrahydrofuran, ter-butanol, ethyl acetate or a combination thereof.

15. The process of claim 14, wherein said solvent is an about 1:1 mixture of acetonitrile and water.

16. The process of claim 1, wherein said oxidizing is performed with a catalytic amount of $RuCl_3$ and about 3 equivalents of $NaBrO_3$ at 40–60° C.

17. The process of claim 5, further comprising dehydrating the composition of claim 2 thereby preparing drospirenone.

* * * * *